United States Patent
Zhang et al.

(10) Patent No.: US 11,517,868 B2
(45) Date of Patent: Dec. 6, 2022

(54) SUBMERGED PROPYLENE HYDRATION MICRO-INTERFACE STRENGTHENING REACTION SYSTEM AND METHOD THEREOF

(71) Applicant: NANJING YANCHANG REACTION TECHNOLOGY RESEARCH INSTITUTE CO., LTD., Nanjing (CN)

(72) Inventors: Zhibing Zhang, Nanjing (CN); Zheng Zhou, Nanjing (CN); Feng Zhang, Nanjing (CN); Lei Li, Nanjing (CN); Weimin Meng, Nanjing (CN); Baorong Wang, Nanjing (CN); Gaodong Yang, Nanjing (CN); Huaxun Luo, Nanjing (CN); Guoqiang Yang, Nanjing (CN); Hongzhou Tian, Nanjing (CN); Yu Cao, Nanjing (CN)

(73) Assignee: NANJING YANCHANG REACTION TECHNOLOGY RESEARCH INSTITUTE CO., LTD., Nanjing (CN)

( * ) Notice: Subject to any disclaimer, the term of this patent is extended or adjusted under 35 U.S.C. 154(b) by 0 days.

(21) Appl. No.: 17/617,949

(22) PCT Filed: May 28, 2020

(86) PCT No.: PCT/CN2020/092755
§ 371 (c)(1),
(2) Date: Dec. 10, 2021

(87) PCT Pub. No.: WO2021/189638
PCT Pub. Date: Sep. 30, 2021

(65) Prior Publication Data
US 2022/0203318 A1    Jun. 30, 2022

(30) Foreign Application Priority Data
Mar. 25, 2020 (CN) .......................... 202010217611.7

(51) Int. Cl.
*B01J 8/00*    (2006.01)
*B01J 8/02*    (2006.01)
(Continued)

(52) U.S. Cl.
CPC ............. *B01J 8/0257* (2013.01); *B01J 8/008* (2013.01); *B01J 8/0285* (2013.01); *C07C 29/48* (2013.01); *B01J 2208/00176* (2013.01)

(58) Field of Classification Search
CPC ....... B01J 8/00; B01J 8/008; B01J 8/02; B01J 8/0242; B01J 8/0257; B01J 8/0285;
(Continued)

(56) References Cited

U.S. PATENT DOCUMENTS 7,910,068 B2 *   3/2011   Hassan ................ B01J 19/0066
                                                                422/129
9,463,427 B1 *  10/2016   Koseoglu ................. B01J 8/008

FOREIGN PATENT DOCUMENTS

CN    101679164 A       3/2010
CN    110591763 A  *   12/2019   ............... B01D 5/00

OTHER PUBLICATIONS

Machine translation of CN 110591763 A, which was published on Sep. 10, 2019. (Year: 2019).*

* cited by examiner

*Primary Examiner* — Natasha E Young

(57) ABSTRACT

A submerged propylene hydration micro-interface strengthening reaction system and a method are proposed. The system includes a reactor, a first micro-interface generator and a second micro-interface generator. Through the micro-interface generators, the propylene is broken to form micron-scale bubbles, which are mixed with reactants and deionized water to form a gas-liquid emulsion, so as to increase a phase boundary area between gas and liquid phases, and achieve a strengthening mass transfer effect (Continued)

under a lower preset operating condition. The micro-scale bubbles can be fully mixed with the deionized water to from a gas-liquid emulsion. By fully mixing gas and liquid phases, it can ensure that the deionized water in the system is in full contact with propylene, and they are fully in contact with the catalyst, which effectively improves the efficiency of preparing isopropanol.

7 Claims, 1 Drawing Sheet

(51) Int. Cl.
    *B01J 19/00*     (2006.01)
    *B01J 19/24*     (2006.01)
    *C07C 29/48*     (2006.01)

(58) Field of Classification Search
    CPC .......... B01J 2208/00; B01J 2208/00008; B01J 2208/00017; B01J 2208/00106; B01J 2208/00168; B01J 2208/00176; B01J 19/00; B01J 19/24; C07C 29/00; C07C 29/48
    See application file for complete search history.

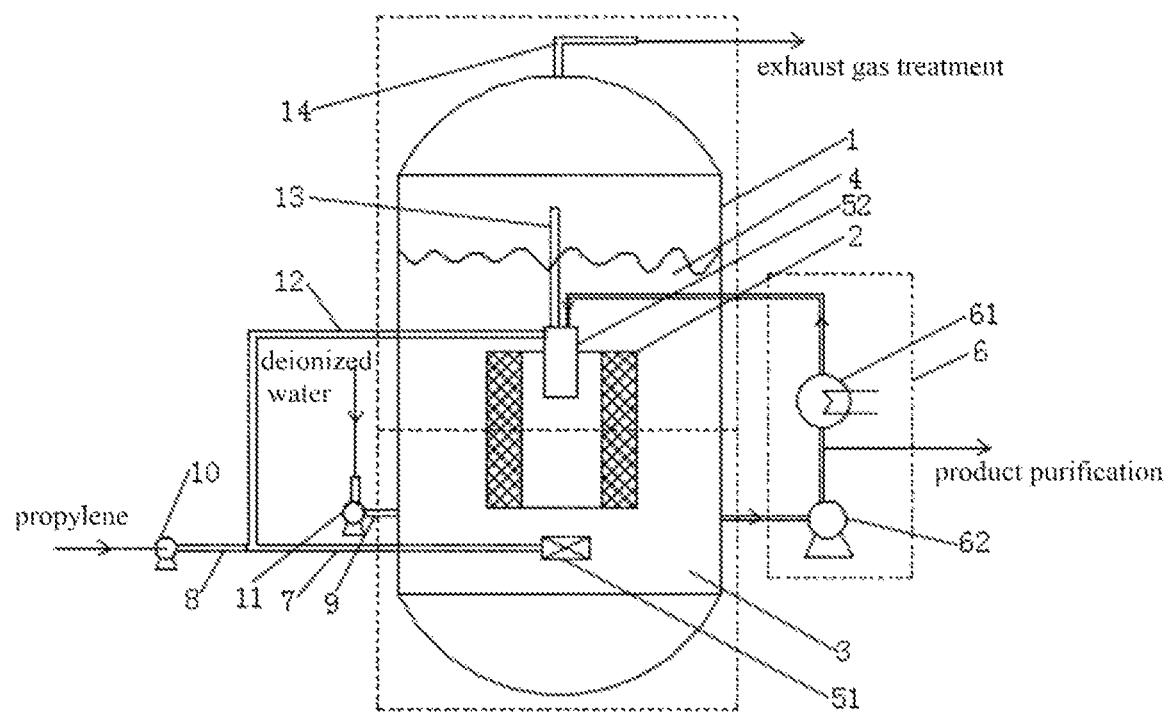

SUBMERGED PROPYLENE HYDRATION MICRO-INTERFACE STRENGTHENING REACTION SYSTEM AND METHOD THEREOF

This application is a national stage application claiming priority to PCT/CN2020/092755, now WO2021/189638, filed on May 28, 2020, which claims priority to Chinese Patent Application Serial No. CN202010217611.7, filed on Mar. 25, 2020.

TECHNICAL FILED

The invention relates to the technical field of isopropanol preparation, in particular, to a submerged propylene hydration micro-interface strengthening reaction system and a method thereof.

BACKGROUND OF THE APPLICATION

An alkene can be converted into a corresponding alcohol by hydration. Common methods mainly include an indirect hydration method and a direct hydration method. The indirect hydration method needs to esterify and hydrolyze the alkene. This reaction uses concentrated sulfuric acid as a medium, has a large consumption amount of concentrated sulfuric acid consumed, has a large treatment amount of waste liquid, and has serious corrosion to equipment. Therefore, the new industrial production device does not use this method basically.

Isopropanol is a colorless, transparent and volatile liquid, is miscible with water, and is also soluble in alcohols, ethers, benzene, and chloroform. Isopropanol is soluble in organic substances such as resins and rubbers, and has odors similar to those of organic substances such as ethanol and acetone. Isopropanol has a wide range of industrial uses, can be used as a chemical raw material to produce isopropyl ether, acetone, hydrogen peroxide, etc., can also be used as a highly efficient solvent to extract effective ingredients from natural substances, and is widely used in industries such as medical production, and can also be used as a gasoline blending additive, a detergent, a dehydrating agent, an anti-freezing agent, etc., and can also be used as a skin care product and be used in the cosmetics industry.

The gas-phase direct hydration method was first developed by the Viba Company in Germany. During the process of producing isopropanol by the existing gas-phase direct hydration method, liquid propylene, deionized water and a recycled propylene gas are introduced into a reactor together with the reaction temperature of 180-260° C. and the reaction pressure of 2-2.5 MPa, the propylene gas reacts with the deionized water under the action of a catalyst to produce isopropanol, and then the reaction product is refined by a procedure such as washing with water and rectification.

The process has a small environmental pollution and is widely applied with respect to a simple process flow of an indirect hydration method. However, the method has obvious disadvantages and disadvantages in use: during a process of contacting propylene gas with deionized water, mixing gas and liquid phases to generate a larger number of bubbles; as there are many and large bubbles, the gas and liquid phases cannot be fully mixed, affecting the contact with the catalyst and reducing the efficiency of preparing isopropanol; and the conversion rate per process of propylene is only 6%-7%.

SUMMARY

In view of this, a submerged propylene hydration micro-interface strengthening reaction system and a method are provided in the present invention to improve the efficiency of preparing isopropanol.

According to an embodiment, a submerged propylene hydration micro-interface strengthening reaction system is provided. The system includes:

a reactor, configured for providing a reaction site for a deionized water and propylene to prepare isopropanol, wherein a catalyst placer is disposed in the reactor, the catalyst placer is in a cylindrical ring shape and is coaxial with the reactor, small holes are respectively and uniformly disposed on an inner side wall and an outer side wall of the catalyst placer, an upper end surface and a lower end surface of the catalyst placer are respectively closed by an annular blind plate, a cavity of the catalyst placer is loaded with a catalyst, the catalyst placer is immersed in a reactant, and the reactor is composed of a fully mixing flow reaction zone and a reflux reaction zone; the fully mixing flow reaction zone is disposed in a bottom of the reactor and is used for loading the deionized water, the propylene and the catalyst and providing a reaction space for a propylene hydration reaction; the reflux reaction zone is disposed in a top of the reactor and is used for refluxing and treating unreacted propylene and reacting the unreacted propylene again with the deionized water;

a micro-interface generator, configured for converting a pressure energy of a gas and/or a kinetic energy of a liquid into a bubble surface energy and for transferring the bubble surface energy to a gas reactant, and for breaking the gas reactant and the propylene to form micron-scale bubbles with a diameter of ≥1 μm and <1 mm, so as to improve a mass transfer area between the gas reactant and a liquid reactant, reduce a thickness of a liquid membrane, and reduce a mass transfer resistance; and a circulating unit, in communication with the reactor and the micro-interface generator, for adjusting a temperature of the reactant in the reactor, providing an entrainment power for the micro-interface generator, and providing a circulating power for the reactant in the reactor to circulate along the catalyst placer to an outside of the catalyst placer, so that the reactant is fully in contact with the catalyst.

Further, the micro-interface generator includes:

a first micro-interface generator, being a pneumatic micro-interface generator, wherein the first micro-interface generator is located in the fully mixing flow reaction zone of the reactor; the first micro-interface generator is used for breaking the propylene to form first micron-scale bubbles, and after the breaking is completed, the first micron-scale bubbles are output to the fully mixing flow reaction zone of the reactor and are mixed with the deionized water in the fully mixing flow reaction zone of the reactor to form a first gas-liquid emulsion; and a second micro-interface generator, being a hydraulic micro-interface generator, wherein the second micro-interface generator is located in a reflux reaction zone in the reactor; the second micro-interface generator is used for breaking and entraining unreacted propylene at an upper portion of the reflux reaction zone of the reactor to form second micron-scale bubbles; the second micron-scale bubbles are mixed with the deionized water to form a second gas-liquid emulsion; and the second gas-liquid emulsion is output to the fully mixing flow reaction zone to perform a butt filtration with the first gas-liquid emulsion output by the first micro-interface generator, so that the unreacted propylene participates in a reaction again.

Further, the inner side wall and the outer side wall of the catalyst placer are composed of stainless steel wire mesh.

Further, the second micro-interface generator is located inside the catalyst placer.

Further, a first propylene transmission pipe, a propylene transmission main pipe and a deionized water transmission pipe are disposed in the fully mixing flow reaction zone, a first pump body is mounted on the propylene transmission main pipe, two ends of the first propylene transmission pipe are respectively connected to the first micro-interface generator and the propylene transmission main pipe, and the first pump body is used for transmitting the propylene to the first micro-interface generator along the propylene transmission main pipe and the first propylene transmission pipe; and a third pump body is disposed in the deionized water transmission pipe, and the third pump body feeds the deionized water into the reactor along the deionized water transmission pipe.

Further, a second propylene transmission pipe, a reflux pipe and an exhaust gas discharge pipe are disposed in the reflux reaction zone; two ends of the second propylene transmission pipe are respectively connected to the propylene transmission main pipe and the second micro-interface generator; one end of the reflux pipe is connected to the second micro-interface generator, the other end of the reflux pipe is located at the upper portion of the reflux reaction zone, and the reflux pipe is used for transferring the unreacted propylene to the second micro-interface generator; and the exhaust gas discharge pipe is used for discharging an exhaust gas in the reactor.

Further the circulating unit includes a heat exchanger and a second pump body; the second pump body is used for pumping a product inside the reactor into the heat exchanger for heat exchange and then discharging the product, providing an entrainment power for the second micro-interface generator, and providing a circulating power for the reactant inside the reactor to circulate along the catalyst placer to the outside of the catalyst placer, so that the reactant is in full contact with the catalyst.

According to another embodiment, a submerged propylene hydration micro-interface strengthening reaction method is provided in the present invention. The method includes the following steps:

Step 1: transmitting, by means of a third pump body, a deionized water along a deionized water transmission pipe into a reactor;

Step 2: transmitting, by means of a first pump body, a propylene to a first micro-interface generator along a propylene transmission main pipe and a first propylene transmission pipe, and simultaneously transmitting the propylene to the second micro-interface generator along the propylene transmission main pipe and a second propylene transmission pipe;

Step 3: operating the first micro-interface generator to break the propylene to form first micron-scale bubbles, and after the breaking is completed, the first micron-scale bubbles are output to a fully mixing flow reaction zone of the reactor and are mixed with the deionized water in the fully mixing flow reaction zone of the reactor so as to form a first gas-liquid emulsion; operating a second micro-interface generator to break and entrain unreacted propylene at an upper portion of the reflux reaction zone of the reactor to form second micron-scale bubbles; the second micron-scale bubbles are mixed with the deionized water to form a second gas-liquid emulsion; and the second gas-liquid emulsion is output to the fully mixing flow reaction zone to perform a butt filtration with the first gas-liquid emulsion output by the first micro-interface generator, so that the unreacted propylene participates in a reaction again; in the reactor, the first gas-liquid emulsion and the second first gas-liquid emulsion generated from the propylene and the deionized water within the reactor are in contact with the catalyst placer and reacted to produce an isopropanol;

Step 4: an exhaust gas in the reactor in the Step 3 is discharged along an exhaust gas discharge pipe, and a subsequent exhaust gas treatment is performed; and Step 5: with generation of the isopropanol in the Step 3, operating a circulation unit to perform a heat exchange treatment on the product, adjusting a temperature of the reactant in the reactor, providing an entrainment power for the micro-interface generator, and providing a circulation power for the reactant in the reactor to circulate along the catalyst placer to an outside of the catalyst placer.

Further, a reaction temperature in the reactor is 170-180° C., and a reaction pressure is 1.7-2.0 MPa.

Compared with the prior art, the beneficial effects of the present invention are as follows: in the present invention, propylene gas is broken to form micron-scale bubbles, and the micron-scale bubbles have physical and chemical properties that conventional bubbles do not have. It can be determined from a calculation formula of a volume and a surface area of a sphere that the total surface area of the bubbles is in inverse proportion to the diameter of a single bubble in the case where the total volume is unchanged. It can be determined therefrom that the total surface area of the micron-scale bubbles is huge, and the micron-scale bubbles are mixed with deionized water to form a gas-liquid emulsion, thereby increasing the contact area of gas and liquid phases, and achieving the effect of strengthening mass transfer in a lower preset operation condition range, and effectively improving the conversion rate and efficiency of preparing isopropanol.

Further, the system includes:

a reactor, configured for providing a reaction site for a deionized water and propylene to prepare isopropanol, wherein a catalyst placer is disposed in the reactor, the catalyst placer is in a cylindrical ring shape and is coaxial with the reactor, small holes are respectively and uniformly disposed on an inner side wall and an outer side wall of the catalyst placer, an upper end surface and a lower end surface of the catalyst placer are respectively closed by an annular blind plate, a cavity of the catalyst placer is loaded with a catalyst, the catalyst placer is immersed in a reactant, and the reactor is composed of a fully mixing flow reaction zone and a reflux reaction zone; the fully mixing flow reaction zone is disposed in a bottom of the reactor and is used for loading the deionized water, the propylene and the catalyst and providing a reaction space for a propylene hydration reaction; the reflux reaction zone is disposed in a top of the reactor and is used for refluxing and treating unreacted propylene and reacting the unreacted propylene again with the deionized water;

a micro-interface generator, configured for converting a pressure energy of a gas and/or a kinetic energy of a liquid into a bubble surface energy and for transferring the bubble surface energy to a gas reactant, and for breaking the gas reactant and the propylene to form micron-scale bubbles with a diameter of $\geq 1$ μm and $<1$ mm, so as to improve a mass transfer area between the gas reactant and a liquid reactant, reduce a thickness of a liquid membrane, and reduce a mass transfer resistance; and a circulating unit, in communication with the reactor and the micro-interface generator, for adjusting a temperature of the reactant in the reactor, providing an entrainment power for the micro-interface generator, and providing a circulating power for the reactant in the reactor to circulate along the catalyst placer to an outside of the catalyst placer, so that the reactant is fully in contact with the catalyst.

Further, the micro-interface generator includes:

a first micro-interface generator, being a pneumatic micro-interface generator, wherein the first micro-interface generator is located in the fully mixing flow reaction zone of the reactor; the first micro-interface generator is used for breaking the propylene to form first micron-scale bubbles, and after the breaking is completed, the first micron-scale bubbles are output to the fully mixing flow reaction zone of the reactor and are mixed with the deionized water in the fully mixing flow reaction zone of the reactor to form a first gas-liquid emulsion; and a second micro-interface generator, being a hydraulic micro-interface generator, wherein the second micro-interface generator is located in a reflux reaction zone in the reactor; the second micro-interface generator is used for breaking and entraining unreacted propylene at an upper portion of the reflux reaction zone of the reactor to form second micron-scale bubbles; the second micron-scale bubbles are mixed with the deionized water to form a second gas-liquid emulsion; and the second gas-liquid emulsion is output to the fully mixing flow reaction zone to perform a butt filtration with the first gas-liquid emulsion output by the first micro-interface generator, so that the unreacted propylene participates in a reaction again.

Further, the inner side wall and the outer side wall of the catalyst placer are composed of stainless steel wire mesh.

Further, the second micro-interface generator is located inside the catalyst placer.

Further, a first propylene transmission pipe, a propylene transmission main pipe and a deionized water transmission pipe are disposed in the fully mixing flow reaction zone, a first pump body is mounted on the propylene transmission main pipe, two ends of the first propylene transmission pipe are respectively connected to the first micro-interface generator and the propylene transmission main pipe, and the first pump body is used for transmitting the propylene to the first micro-interface generator along the propylene transmission main pipe and the first propylene transmission pipe; and a third pump body is disposed in the deionized water transmission pipe, and the third pump body feeds the deionized water into the reactor along the deionized water transmission pipe.

Further, a second propylene transmission pipe, a reflux pipe and an exhaust gas discharge pipe are disposed in the reflux reaction zone; two ends of the second propylene transmission pipe are respectively connected to the propylene transmission main pipe and the second micro-interface generator; one end of the reflux pipe is connected to the second micro-interface generator, the other end of the reflux pipe is located at the upper portion of the reflux reaction zone, and the reflux pipe is used for transferring the unreacted propylene to the second micro-interface generator; and the exhaust gas discharge pipe is used for discharging an exhaust gas in the reactor.

Further the circulating unit includes a heat exchanger and a second pump body; the second pump body is used for pumping a product inside the reactor into the heat exchanger for heat exchange and then discharging the product, providing an entrainment power for the second micro-interface generator, and providing a circulating power for the reactant inside the reactor to circulate along the catalyst placer to the outside of the catalyst placer, so that the reactant is in full contact with the catalyst.

BRIEF DESCRIPTION OF DRAWINGS

By reading the detailed description of the preferred embodiments below, various other advantages and benefits will become clear to those of ordinary skill in the art. The drawings are only used for the purpose of illustrating the preferred embodiments, and are not considered as a limitation to the invention. Also, throughout the drawings, the same reference numerals are used to denote the same components. In the drawings:

FIG. 1 is a structural diagram of a submerged propylene hydration micro-interface strengthening reaction system according to an embodiment of the present invention.

DETAIL DESCRIPTION

In order to make the purpose and advantages of the invention clearer, the invention will be further described below in conjunction with the embodiments. It should be understood that the specific embodiments described here are only used to explain the invention, and are not used to limit the invention.

It should be understood that in the description of the invention, orientations or position relationships indicated by terms upper, lower, front, back, left, right, inside, outside and the like are orientations or position relationships are based on the direction or position relationship shown in the drawings, which is only for ease of description, rather than indicating or implying that the device or element must have a specific orientation, be constructed and operated in a specific orientation, and therefore cannot be understood as a limitation of the invention. In addition, the terms "first", "second", and "third" are only used for descriptive purposes, and cannot be understood as indicating or implying relative importance.

Further, it should also be noted that in the description of the invention, terms "mounting", "connected" and "connection" should be understood broadly, for example, may be fixed connection and also may be detachable connection or integral connection; may be mechanical connection and also may be electrical connection; and may be direct connection, also may be indirection connection through an intermediary, and also may be communication of interiors of two components. Those skilled in the art may understand the specific meaning of terms in the invention according to specific circumstance.

Referring to FIG. 1, the present invention provides a submerged propylene hydration micro-interface strengthening reaction system, including:

A reactor 1 used for providing a reaction site for deionized water and propylene to prepare isopropanol, wherein a catalyst placer 2 is disposed in the reactor 1. The catalyst placer 2 is in a cylindrical ring shape and is coaxial with the reactor 1, small holes are respectively and uniformly disposed on an inner side wall and an outer side wall of the catalyst placer 2, an upper end surface and a lower end surface of the catalyst placer 2 are respectively closed by an annular blind plate, a cavity of the catalyst placer 2 is loaded with a catalyst, the catalyst placer 2 is immersed in a reactant, and the reactor 1 is composed of a fully mixing flow reaction zone 3 and a reflux reaction zone 4. The fully mixing flow reaction zone 3 is disposed in a bottom of the reactor 1 and is used for loading deionized water, propylene and a catalyst and providing a reaction space for a propylene hydration reaction. The reflux reaction zone 3 is disposed in a top of the reactor 1 and is used for refluxing and treating unreacted propylene and reacting the unreacted propylene again with deionized water.

A micro-interface generator converts pressure energy of a gas and/or kinetic energy of a liquid into bubble surface energy and transfers the bubble surface energy to a gas reactant, and breaks the gas reactant propylene to form micron-scale bubbles with a diameter of ≥1 µm and <1 mm, so as to improve the mass transfer area between the gas reactant and the liquid reactant, reduce the thickness of the liquid membrane, and reduce the mass transfer resistance.

A circulating unit 6 is in communication with the reactor 1 and the micro-interface generator for adjusting the temperature of a reactant in the reactor 1, providing an entrainment power for the micro-interface generator, and providing a circulating power for the reactant in the reactor 1 to circulate along the catalyst placer 2 to the outside of the catalyst placer 2, so that the reactant is fully in contact with the catalyst.

Referring to FIG. 1 again, the micro-interface generator includes:

A first micro-interface generator 51, being a pneumatic micro-interface generator, wherein the first micro-interface generator 51 is located in the fully mixing flow reaction zone 3 of the reactor 3. The first micro-interface generator 51 is used for breaking propylene to form first micron-scale bubbles, and after the breaking is completed, the first micron-scale bubbles are output to the fully mixing flow reaction zone 3 of the reactor 1 and are mixed with deionized water in the fully mixing flow reaction zone 3 of the reactor 1 to form a first gas-liquid emulsion. A second micro-interface generator 52 being a hydraulic micro-interface generator, wherein the second micro-interface generator 52 is located in the reflux reaction zone 4 of the reactor 1. The second micro-interface generator 52 is used for breaking and entraining unreacted propylene at the upper portion of the reflux reaction zone 4 of the reactor 1 to form second micron-scale bubbles. The second micron-scale bubbles are mixed with deionized water to form a second gas-liquid emulsion. The second gas-liquid emulsion is output to the fully mixing flow reaction zone 3 to perform a butt filtration with the first gas-liquid emulsion output by the first micro-interface generator 51, so that the unreacted propylene participates in a reaction again.

Referring to FIG. 1 again, the inner side wall and the outer side wall of the catalyst placer are composed of stainless steel wire mesh.

Referring to FIG. 1 again, the second micro-interface generator 52 is located inside the catalyst placer 2.

Referring to FIG. 1 again, a first propylene transmission pipe 7, a propylene transmission main pipe 8 and a deionized water transmission pipe 9 are disposed in the fully mixing flow reaction zone 3. A first pump body 10 is mounted on the propylene transmission main pipe 8, and two ends of the first propylene transmission pipe 7 are respectively connected to the first micro-interface generator 51 and the propylene transmission main pipe 8. The first pump body 10 is used for transmitting propylene to the first micro-interface generator 51 along the propylene transmission main pipe 8 and the first propylene transmission pipe 7. A third pump body 11 is disposed in the deionized water transmission pipe 9, and the third pump body 11 feeds deionized water into the reactor 1 along the deionized water transmission pipe 9.

Referring to FIG. 1 again, a second propylene transmission pipe 12, a reflux pipe 13 and an exhaust gas discharge pipe 14 are disposed in the reflux reaction zone 4. Two ends of the second propylene transmission pipe 12 are respectively connected to the propylene transmission main pipe 8 and the second micro-interface generator 52. One end of the reflux pipe 13 is connected to the second micro-interface generator 52, the other end of the reflux pipe 13 is located at the upper portion of the reflux reaction zone 4, and the reflux pipe 13 is used for transferring unreacted propylene to the second micro-interface generator 52. The exhaust gas discharge pipe 14 is used for discharging the exhaust gas in the reactor 1.

Referring to FIG. 1 again, the circulating unit 6 includes a heat exchanger 61 and a second pump body 62. The second pump body 62 is used for pumping the product inside the reactor 1 into the heat exchanger 61 for heat exchange and then discharging the product, providing an entrainment power for the second micro-interface generator 52, and providing a circulating power for the reactant inside the reactor 1 to circulate along the catalyst placer 2 to the outside of the catalyst placer 2, so that the reactant is in full contact with the catalyst.

Referring to FIG. 1 again, the catalyst is a diatomite catalyst with a phosphoric acid loading of 20 wt %-30 wt %.

Referring to FIG. 1 again, the present invention provides a submerged propylene hydration micro-interface strengthening reaction method, including:

Step 1: transmitting, by means of a third pump body, a deionized water along a deionized water transmission pipe into a reactor;

Step 2: transmitting, by means of a first pump body, a propylene to a first micro-interface generator along a propylene transmission main pipe and a first propylene transmission pipe, and simultaneously transmitting the propylene to the second micro-interface generator along the propylene transmission main pipe and a second propylene transmission pipe;

Step 3: operating the first micro-interface generator to break the propylene to form first micron-scale bubbles, and after the breaking is completed, the first micron-scale bubbles are output to a fully mixing flow reaction zone of the reactor and are mixed with the deionized water in the fully mixing flow reaction zone of the reactor so as to form a first gas-liquid emulsion; operating a second micro-interface generator to break and entrain unreacted propylene at an upper portion of the reflux reaction zone of the reactor to form second micron-scale bubbles; the second micron-scale bubbles are mixed with the deionized water to form a second gas-liquid emulsion; and the second gas-liquid emulsion is output to the fully mixing flow reaction zone to perform a butt filtration with the first gas-liquid emulsion output by the first micro-interface generator, so that the unreacted propylene participates in a reaction again; in the reactor, the first gas-liquid emulsion and the second first gas-liquid emulsion generated from the propylene and the deionized water within the reactor are in contact with the catalyst placer and reacted to produce an isopropanol;

Step 4: an exhaust gas in the reactor in the Step 3 is discharged along an exhaust gas discharge pipe, and a subsequent exhaust gas treatment is performed; and Step 5: with generation of the isopropanol in the Step 3, operating a circulation unit to perform a heat exchange treatment on the product, adjusting a temperature of the reactant in the reactor, providing an entrainment power for the micro-interface generator, and providing a circulation power for the reactant in the reactor to circulate along the catalyst placer to an outside of the catalyst placer.

Further, the reactor has a temperature of 170-180° C. and a pressure of 1.7-2.0 MPa.

Example 1

Isopropanol is prepared by using the abovementioned system and method, wherein the reactor temperature is 170° C., and the pressure inside the reactor is 1.7 MPa. The gas-liquid ratio in the first micro-interface generator 51 is 800:1; and the gas-liquid ratio in the second micro-interface generator 52 is 3:1000.

Upon detection, the conversion per pass of propylene is 26% by using the abovementioned system and method.

Example 2

Isopropanol is prepared by using the abovementioned system and method, wherein the reactor temperature is 175° C., and the pressure inside the reactor is 1.8 MPa. The gas-liquid ratio in the first micro-interface generator 51 is 800:1; and the gas-liquid ratio in the second micro-interface generator 52 is 3:1000.

Upon detection, the conversion per pass of propylene is 26% by using the abovementioned system and method.

Example 3

Isopropanol is prepared by using the abovementioned system and method, wherein the reactor temperature is 176° C., and the pressure inside the reactor is 1.9 MPa. The gas-liquid ratio in the first micro-interface generator is 800:1; and the gas-liquid ratio in the second micro-interface generator is 3:1000.

Upon detection, the conversion per pass of propylene is 26% by using the abovementioned system and method.

Example 4

Isopropanol is prepared by using the abovementioned system and method, wherein the reactor temperature is 178° C., and the pressure inside the reactor is 2.0 MPa. The gas-liquid ratio in the first micro-interface generator is 800:1; and the gas-liquid ratio in the second micro-interface generator is 3:1000.

Upon detection, the conversion per pass of propylene is 27% by using the abovementioned system and method.

Example 5

Isopropanol is prepared by using the abovementioned system and method, wherein the reactor temperature is 180° C., and the pressure inside the reactor is 2.0 MPa. The gas-liquid ratio in the first micro-interface generator is 800:1; and the gas-liquid ratio in the second micro-interface generator is 3:1000.

Upon detection, the conversion per pass of propylene is 27% by using the abovementioned system and method.

Comparative Example

Isopropanol is prepared by a direct propylene hydration method in the prior art, in which process parameters selected in this Comparative Example are the same as those in Example 5.

Upon detection, the conversion per pass of propylene is 6%.

So far, the technical solution of the invention has been described in conjunction with the preferred embodiments shown in the drawings. However, it is easily understood by those skilled in the art that the protection scope of the invention is obviously not limited to these specific embodiments. Without departing from the principle of the invention, those skilled in the art can make equivalent changes or substitutions to the relevant technical features, which will fall into the protection scope of the invention. The above are only preferred embodiments of the invention rather than limits to the invention. Those skilled in the art may make various modifications and changes to the invention. Any modification, equivalent replacement, improvement and the like made within the spirit and principle of the invention all should be included in the protection scope of the invention.

The invention claimed is:

1. A submerged propylene hydration micro-interface strengthening reaction system, comprising:
a reactor, configured for providing a reaction site for a deionized water and propylene to prepare isopropanol, wherein a catalyst placer is disposed in the reactor, the catalyst placer is in a cylindrical ring shape and is coaxial with the reactor, small holes are respectively and uniformly disposed on an inner side wall and an outer side wall of the catalyst placer, an upper end surface and a lower end surface of the catalyst placer are respectively closed by an annular blind plate, a cavity of the catalyst placer is loaded with a catalyst, the catalyst placer is immersed in a reactant, and the reactor is composed of a fully mixing flow reaction zone and a reflux reaction zone; the fully mixing flow reaction zone is disposed in a bottom of the reactor and is used for loading the deionized water, the propylene and the catalyst and providing a reaction space for a propylene hydration reaction; the reflux reaction zone is disposed in a top of the reactor and is used for refluxing and treating unreacted propylene and reacting the unreacted propylene again with the deionized water;
a micro-interface generator, configured for converting a pressure energy of a gas and/or a kinetic energy of a liquid into a bubble surface energy and for transferring the bubble surface energy to a gas reactant, and for breaking the gas reactant and the propylene to form micron-scale bubbles with a diameter of ≥1 µm and <1 mm, so as to improve a mass transfer area between the gas reactant and a liquid reactant, reduce a thickness of a liquid membrane, and reduce a mass transfer resistance;
wherein the micro-interface generator comprises:
a first micro-interface generator, being a pneumatic micro-interface generator, wherein the first micro-interface generator is located in the fully mixing flow reaction zone of the reactor; the first micro-interface generator is used for breaking the propylene to form first micron-scale bubbles, and after the breaking is completed, the first micron-scale bubbles are output to the fully mixing flow reaction zone of the reactor and are mixed with the deionized water in the fully mixing flow reaction zone of the reactor to form a first gas-liquid emulsion; and
a second micro-interface generator, being a hydraulic micro-interface generator, wherein the second micro-interface generator is located in a reflux reaction zone in the reactor; the second micro-interface generator is used for breaking and entraining unreacted propylene at an upper portion of the reflux reaction zone of the reactor to form second micron-scale bubbles; the second micron-scale bubbles are mixed with the deionized water to form a second gas-liquid emulsion; and the second gas-liquid emulsion is output to the fully mixing flow reaction zone to perform a butt filtration with the first gas-liquid emulsion output by the first micro-interface generator, so that the unreacted propylene participates in a reaction again;

wherein the second micro-interface generator is located inside the catalyst placer; and a circulating unit, in communication with the reactor and the micro-interface generator, for adjusting a temperature of the reactant in the reactor, providing an entrainment power for the micro-interface generator, and providing a circulating power for the reactant in the reactor to circulate along the catalyst placer to an outside of the catalyst placer, so that the reactant is fully in contact with the catalyst.

2. The submerged propylene hydration micro-interface strengthening reaction system according to claim 1, wherein the inner side wall and the outer side wall of the catalyst placer are composed of stainless steel wire mesh.

3. The submerged propylene hydration micro-interface strengthening reaction system according to claim 1, wherein a first propylene transmission pipe, a propylene transmission main pipe and a deionized water transmission pipe are disposed in the fully mixing flow reaction zone, a first pump body is mounted on the propylene transmission main pipe, two ends of the first propylene transmission pipe are respectively connected to the first micro-interface generator and the propylene transmission main pipe, and the first pump body is used for transmitting the propylene to the first micro-interface generator along the propylene transmission main pipe and the first propylene transmission pipe; and a third pump body is disposed in the deionized water transmission pipe, and the third pump body feeds the deionized water into the reactor along the deionized water transmission pipe.

4. The submerged propylene hydration micro-interface strengthening reaction system according to claim 3, wherein a second propylene transmission pipe, a reflux pipe and an exhaust gas discharge pipe are disposed in the reflux reaction zone; two ends of the second propylene transmission pipe are respectively connected to the propylene transmission main pipe and the second micro-interface generator; one end of the reflux pipe is connected to the second micro-interface generator, the other end of the reflux pipe is located at the upper portion of the reflux reaction zone, and the reflux pipe is used for transferring the unreacted propylene to the second micro-interface generator; and the exhaust gas discharge pipe is used for discharging an exhaust gas in the reactor.

5. The submerged propylene hydration micro-interface strengthening reaction system according to claim 4, wherein the circulating unit comprises a heat exchanger and a second pump body; the second pump body is used for pumping a product inside the reactor into the heat exchanger for heat exchange and then discharging the product, providing an entrainment power for the second micro-interface generator, and providing a circulating power for the reactant inside the reactor to circulate along the catalyst placer to the outside of the catalyst placer, so that the reactant is in full contact with the catalyst.

6. A submerged propylene hydration micro-interface strengthening reaction method, comprising:

Step 1: transmitting, by means of a third pump body, a deionized water along a deionized water transmission pipe into a reactor;

Step 2: transmitting, by means of a first pump body, a propylene to a first micro-interface generator along a propylene transmission main pipe and a first propylene transmission pipe, and simultaneously transmitting the propylene to the second micro-interface generator along the propylene transmission main pipe and a second propylene transmission pipe;

Step 3: operating the first micro-interface generator to break the propylene to form first micron-scale bubbles, and after the breaking is completed, the first micron-scale bubbles are output to a fully mixing flow reaction zone of the reactor and are mixed with the deionized water in the fully mixing flow reaction zone of the reactor so as to form a first gas-liquid emulsion; operating a second micro-interface generator to break and entrain unreacted propylene at an upper portion of the reflux reaction zone of the reactor to form second micron-scale bubbles; the second micron-scale bubbles are mixed with the deionized water to form a second gas-liquid emulsion; and the second gas-liquid emulsion is output to the fully mixing flow reaction zone to perform a butt filtration with the first gas-liquid emulsion output by the first micro-interface generator, so that the unreacted propylene participates in a reaction again; in the reactor, the first gas-liquid emulsion and the second first gas-liquid emulsion generated from the propylene and the deionized water within the reactor are in contact with a catalyst placer and reacted to produce an isopropanol;

Step 4: an exhaust gas in the reactor in the Step 3 is discharged along an exhaust gas discharge pipe, and a subsequent exhaust gas treatment is performed; and Step 5: with generation of the isopropanol in the Step 3, operating a circulation unit to perform a heat exchange treatment on the product, adjusting a temperature of the reactant in the reactor, providing an entrainment power for the micro-interface generator, and providing a circulation power for the reactant in the reactor to circulate along the catalyst placer to an outside of the catalyst placer.

7. The submerged propylene hydration micro-interface strengthening reaction method according to claim 6, wherein a reaction temperature in the reactor is 170-180° C., and a reaction pressure is 1.7-2.0 MPa.

* * * * *